(12) United States Patent
Martin

(10) Patent No.: US 6,942,896 B1
(45) Date of Patent: Sep. 13, 2005

(54) ELASTIC NONWOVEN SHEET

(75) Inventor: Kenneth E. Martin, Newark, DE (US)

(73) Assignee: INVISTA North America S.a.r.l., Wilmington, DE (US)

( * ) Notice: Subject to any disclaimer, the term of this patent is extended or adjusted under 35 U.S.C. 154(b) by 255 days.

(21) Appl. No.: 10/413,172

(22) Filed: Apr. 14, 2003

Related U.S. Application Data

(60) Provisional application No. 60/372,911, filed on Apr. 15, 2002.

(51) Int. Cl.$^7$ ............................. B05D 3/10; B05D 3/12
(52) U.S. Cl. ...................................... 427/336; 427/368
(58) Field of Search .................................. 427/336, 368

(56) References Cited

U.S. PATENT DOCUMENTS

| | | | |
|---|---|---|---|
| 4,366,814 A | 1/1983 | Riedel | |
| 4,443,513 A | 4/1984 | Meitner et al. | |
| 4,613,537 A * | 9/1986 | Krupper | 428/192 |
| 4,965,122 A | 10/1990 | Morman | |
| 4,981,747 A | 1/1991 | Morman | |
| 5,114,781 A | 5/1992 | Morman | |
| RE35,206 E | 4/1996 | Hassenboehler, Jr. et al. | |
| 5,910,224 A | 6/1999 | Morman | |
| 6,623,837 B2 * | 9/2003 | Morman et al. | 428/152 |

FOREIGN PATENT DOCUMENTS

| | | |
|---|---|---|
| EP | 0 161 515 A1 | 11/1985 |
| EP | 0 341 430 A1 | 11/1989 |
| EP | 0 432-755 A1 | 6/1991 |
| EP | 0 523 806 A1 | 1/1993 |
| EP | 0 472 942 | 9/1995 |
| EP | 672777 * | 9/1995 |
| EP | 0 969 139 A2 | 1/2000 |
| JP | SHO 47-24479 | 7/1972 |
| JP | 7 097461 A | 4/1995 |

* cited by examiner

Primary Examiner—Erma Cameron
(74) Attorney, Agent, or Firm—Robert B. Furr, Jr.

(57) ABSTRACT

This invention relates to stretchable nonwoven sheets prepared by substantially uniformly impregnating a necked nonwoven substrate with an elastomeric polymer by treatment with an elastomeric polymer solution. The nonwoven sheet is useful in the manufacture of diapers and other hygiene articles.

6 Claims, No Drawings

ELASTIC NONWOVEN SHEET

BACKGROUND OF THE INVENTION

1. Field of the Invention

This invention relates to stretchable nonwoven sheets suitable for use in the manufacture of personal hygiene articles. More specifically, the stretchable nonwoven sheets are formed by substantially uniformly impregnating a necked nonwoven substrate with an elastomeric polymer.

2. Description of Related Art

Elastic nonwoven materials are well known in the art. Examples of elastic nonwoven materials include "stretch-bonded" and "neck-bonded" laminates. Stretch-bonded laminates are prepared by joining a gatherable layer to an elastic layer while the elastic layer is in an extended condition so that upon relaxing the layers, the gatherable layer is gathered. Neck-bonded laminates are produced by joining a necked, non-elastic layer with an elastic film on fiber layer. The elastic layer generally comprises an elastic film or an elastic nonwoven web. These elastic nonwoven laminates require the preparation of at least two separate nonwoven or film layers.

U.S. Pat. No. 4,366,814 to Riedel (Riedel) describes a breathable elastic bandage material comprising at least 50 weight percent of an extensible fabric capable of an elongation of at least 30% without tearing and at least 15 weight percent of an elastomer impregnated in the fabric without filling the holes in the fabric.

U.S. Pat. No. 5,910,224 to Morman (Morman) describes a method for making a stretchable composite by applying an elastomeric precursor to a neckable material such as a nonwoven web, neck stretching the neckable material and treating the elastomeric precursor, such as by heating, while the neckable material is in a necked condition to form an elastomeric layer bonded to the necked material. Preferred elastomeric precursors comprise a latex or a thermoset elastomer. The elastomeric precursor is applied to the neckable material in an amount between 5 g/m$^2$ to about 50 g/m$^2$. The elastomeric layer preferably penetrates the web from about 2 to about 10 fiber thicknesses and the degree of penetration of the elastomeric precursor is controlled so that there is no strikethrough to the side of the web opposite the side on which the elastomeric layer has been applied. The resulting stretchable composite therefore has a film-like hand on the side comprising the elastomeric layer and retains the original soft hand of the neckable material on the side opposite the elastomeric layer.

Published European Patent Application No. 0472942 describes an elastomeric saturated nonwoven material having a compressibility and recovery in the Z-direction which includes a fibrous web, such as a nonwoven web of melt-blown fibers, that is saturated with a polymeric material, such as an elastomeric acrylic latex, polyurethane latex, or nitrile rubber latex.

Published Japanese Patent Application No. 47-24479 is directed to belts for use in conveyors and power transmissions that are made by impregnating needlepunched nonwoven fabrics with rubber or synthetic resins.

There is a continued need for elastic sheet materials that can be produced economically, have soft stretch and good holding power, and which have a fabric-like hand on both surfaces.

BRIEF SUMMARY OF THE INVENTION

The subject invention is directed to a method for forming a stretchable nonwoven sheet comprising the steps of:

providing a necked nonwoven substrate having a thickness, first and second outer surfaces, a machine direction and a cross-direction, the necked nonwoven substrate having a percent elongation of at least 30% in the cross-direction;

substantially uniformly impregnating the necked nonwoven substrate with a solution comprising an elastomeric polymer dissolved in a solvent; and removing the solvent from the impregnated nonwoven substrate by wet coagulation to deposit the elastomeric polymer substantially uniformly throughout the thickness of the nonwoven substrate without forming a substantially continuous layer of elastomeric polymer on either of the first or second outer surfaces of the nonwoven substrate.

The subject invention is also directed to a stretchable nonwoven sheet comprising a nonwoven substrate that has been necked in a necked direction and substantially uniformly impregnated with an elastomeric polymer, the stretchable nonwoven sheet having a ratio of third unload cycle force at 100% elongation to third load cycle force at 100% elongation, after the stretchable nonwoven sheet has been extended to 140% in the necked direction three times, of at least 0.3:1.

DETAILED DESCRIPTION OF THE INVENTION

In the current invention, a stretchable composite nonwoven sheet is provided by impregnating a necked nonwoven substrate with a solution comprising a solvent and an elastomeric polymer. The necked nonwoven substrate is impregnated under conditions that achieve substantially uniform impregnation of the nonwoven substrate without forming a polymer layer on either surface thereof. After removal of the solvent, a breathable impregnated nonwoven sheet is obtained which has an unexpected combination of high unload cycle force compared to load cycle force (for good holding power and soft stretch) in the cross-direction and a textile-like hand. Further, the inventive sheet is typically simpler to make and thinner than conventional multilayer stretch laminates. For example, the inventive sheet can have a typical thickness of about 0.25 mm to 0.75 mm, whereas stretch laminates are generally thicker than 1.3 mm.

The term "polymer" as used herein, generally includes but is not limited to, homopolymers, copolymers (such as for example, block, graft, random and alternating copolymers), terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

The term "polyester" as used herein is intended to embrace polymers wherein at least 85% of the recurring units are condensation products of dicarboxylic acids and dihydroxy alcohols with linkages created by formation of ester units. This includes aromatic, aliphatic, saturated, and unsaturated di-acids and di-alcohols. The term "polyester" as used herein also includes copolymers (such as block, graft, random and alternating copolymers), blends, and modifications thereof. A common example of a polyester is poly(ethylene terephthalate) (PET) which is a condensation product of ethylene glycol and terephthalic acid.

The term "polyurethane" as used herein is intended to include block copolymers made by condensing a difunctional polyol with a diisocyanate and a difunctional chain extender, as described in detail hereinbelow.

The term "polyolefin" as used herein, is intended to mean any of a series of largely saturated open chain polymeric hydrocarbons composed only of carbon and hydrogen. Typical polyolefins include, but are not limited to, polyethylene, polypropylene, polymethylpentene and various combinations of the ethylene, propylene, and methylpentene monomers.

The term "polyethylene" as used herein is intended to encompass not only homopolymers of ethylene, but also copolymers wherein at least 85% of the recurring units are ethylene units.

The term "polypropylene" as used herein is intended to embrace not only homopolymers of propylene but also copolymers where at least 85% of the recurring units are propylene units.

The term "elastomeric polymer" as used herein refers to any polymer that, when formed into a sheet, fiber, or film and upon application of a biasing force, is elongatable to a stretched length that is at least about 160 percent of its relaxed unbiased length and that will recover at least 55 percent of its elongation upon release of the elongating biasing force. For example, a one centimeter sample of material that is elongatable to at least 1.6 centimeters and which, upon being elongated to 1.6 centimeters by application of a force and with release of the force, will recover to a length of not more than 1.27 centimeters. Many elastomeric materials exist which may be stretched by much more than 60% of their relaxed length, for example 100, percent or more, and many of these will recover to substantially their original relaxed length, for example, to within 105 percent of their original relaxed length, upon release of the stretching force.

The terms "nonwoven fabric" or "nonwoven web" as used herein mean a structure of individual fibers, filaments, or threads that are positioned in a random manner to form a planar material without an identifiable pattern, as opposed to a knifted or woven fabric.

The term "spunbond" filaments as used herein means filaments which are formed by extruding molten thermoplastic polymer material as filaments from a plurality of fine, usually circular, capillaries of a spinneret with the diameter of the extruded filaments then being rapidly reduced by drawing. Other filament cross-sectional shapes such as oval, multi-lobal, etc. can also be used. Spunbond filaments are generally continuous and have an average diameter of greater than about 5 micrometers. Spunbond nonwoven fabrics or webs are formed by laying spunbond filaments randomly on a collecting surface such as a foraminous screen or belt. Spunbond webs are generally bonded by methods known in the art, such as hot-roll calendering or passing the web through a saturated-steam chamber at an elevated pressure. Also, the web can be thermally point bonded at a plurality of thermal bond points located across the spunbond fabric.

The term "machine direction" (MD) is used herein to refer to the direction in which a nonwoven web is produced. The term "cross direction" (XD) refers to the direction generally perpendicular to the machine direction.

The term "necking" as used herein refers to a method which involves applying a force to a nonwoven fabric, for example parallel to the machine direction of the nonwoven, to cause the nonwoven fabric to elongate in the direction the force is applied and to reduce its width in the direction perpendicular to that of the elongation, for example in the cross-direction, in a controlled manner to a desired amount. The direction perpendicular to the elongating force is referred to herein as the "necked direction". The controlled stretching and necking may take place at room temperature or at temperatures higher or lower than room temperature and is limited to an increase in overall dimension in the direction being stretched up to the elongation required to tear or break the fabric.

The terms "necked nonwoven fabric" and "necked nonwoven substrate" are used herein to refer to any nonwoven fabric which has been constricted in at least one direction by processes such as drawing. A "neckable nonwoven fabric" is a nonwoven fabric that can be constricted in at least one dimension in a necking process. The term "percent neckdown" refers to the ratio determined by measuring the difference between the un-necked dimension and the necked dimension (measured in the necked direction) and then dividing the difference by the un-necked dimension and multiplying the resulting ratio by 100. Necked nonwovens are generally extensible in the necked direction by an amount corresponding (but not a linear relationship) to the percent neckdown during necking. The extensibility of a necked nonwoven is measured herein as the percent elongation by elongating a necked nonwoven in the necked direction to the maximum extent possible without elongating individual fibers within the nonwoven, disrupting any fiber-to-fiber bonds within the nonwoven or tearing the nonwoven.

The term "wet coagulation" is used herein to describe a process in which a nonwoven substrate, having impregnated therein a solution comprising an elastomeric polymer dissolved in a solvent, is contacted with a coagulating liquid which is a non-solvent for the elastomeric polymer but is miscible with the solvent used to form the elastomeric polymer solution. The coagulating liquid is also selected such that it does not dissolve the nonwoven substrate. The coagulating liquid causes the polymeric material to be coagulated and the solvent to be removed into the coagulating liquid. The coagulating liquid is subsequently removed from the polymer-impregnated nonwoven, such as by air drying or heating.

Neckable nonwoven fabrics suitable for use in the current invention include spunbond webs, bonded carded webs, and hydroentangled webs. The neckable nonwoven fabric is preferably necked in the cross-direction using methods known in the art to achieve a percent neckdown of between about 25% and about 75% to obtain a necked nonwoven substrate having a percent elongation in the cross-direction of between about 30% and about 300%. Neckable nonwoven fabrics useful in the current invention may be made from a number of thermoplastic polymers including non-elastomeric polyolefins such as polyethylene, polypropylene, ethylene copolymers, polyamides, polyesters, polystyrene, and poly-4-methylpentene-1. Preferably the neckable nonwoven fabric comprises polypropylene, polyester, or a polypropylene-polyethylene copolymer. In a preferred embodiment, the neckable nonwoven fabric is a spunbond polypropylene fabric or carded thermal bond polypropylene or polyester fabric. The starting neckable nonwoven substrate preferably has a basis weight between about 10 g/m$^2$ and about 50 g/m$^2$. Relatively low basis weight neckable nonwovens are especially preferred such as those having a basis weight between about 10 g/m$^2$ and about 20 g/m$^2$. The nonwoven substrate is preferably moisture vapor permeable.

The neckable nonwoven substrates are necked to provide necked nonwoven substrates generally having a basis weight greater than about 15 g/m².

Necked nonwoven fabrics are known in the art and are generally prepared by elongating a neckable nonwoven fabric in the machine direction to provide a necked nonwoven fabric that is necked in the cross direction. Examples of necking processes are disclosed, for example, in U.S. Pat. No. 4,443,513 to Meitner et al. (Meitner), U.S. Pat. Nos. 4,965,122, 4,981,747, and 5,114,781 (all to Morman). A preferred necking process is disclosed in U.S. Re 35,206 to Hassenboehler Jr. et al. (Hassenboehler). U.S. Re 35,206 is a reissue of U.S. Pat. No. 5,244,482 and is hereby incorporated by reference. A nonwoven web that has been necked according to the process of Hassenboehler is also referred to herein as a "consolidated web".

Necked nonwovens can be prepared using relatively low cost processes and are preferred over other extensible nonwoven fabrics because they have a higher degree of cross-direction extensibility and require relatively low extension (load) forces to extend the nonwoven in the cross-direction. In addition, necked nonwoven fabrics are generally substantially inextensible in the machine direction, that is they have a percent elongation of less than about 5% when subjected to a biasing force in the machine direction. Stretch in substantially one direction is highly desirable in certain end uses as discussed below.

In a preferred embodiment, the necked nonwoven substrate is a consolidated web prepared using the method described in Hassenboehler. This method involves passing a bonded thermoplastic nonwoven web having relatively low processing extensibility through a heated zone, such as an oven, to increase the temperature of the web to a temperature between the polymeric web's softening temperature and melting temperature while drawing the web in the machine direction thereby plastically deforming the fibers oriented in the cross-direction and consolidating (necking) the web in the cross direction. The drawing is conducted by passing the web into the zone at a first linear velocity and withdrawing it at a second linear velocity that exceeds the first velocity. The ratio of the second velocity to the first velocity is preferably in the range from about 1.1:1 to about 2:1. The starting bonded nonwoven web is a non-elastomeric neckable nonwoven fabric and is selected to have a breaking draw ratio during hot processing of less than about 4.0:1 and greater than about 1.4:1 evaluated while hot drawing at a strain rate greater than 2500%/min and a temperature greater than the softening point, but at least 10° F. less than the melting temperature of the polymeric web. The room temperature elongation (strain) at break is preferably between 2 and 40 percent, more preferably between 5 and 20 percent, based on test method ASTM D 1117–77 using an Instron tensile testing machine.

The fibers in the starting web may be bonded by fiber-to-fiber fusion, fiber entanglement, or thermal bonds such as by point bonding. Preferably, the fibers in the neckable nonwoven fabric have small average fiber diameters, for example less than about 50 micrometers. The bonding in the spunbond precursor is preferably strong (e.g. high temperature point bonding) in order to locally elongate, buckle, and bend the filament segments without affecting the web integrity. In point bonding, the bond points and bonding pattern are generally selected such that the area of the bonding points is between about 5 and about 25% of the web area. The shape of the bonding points can be diamond shaped or a number of other shapes well known in the art.

The heated drawing step causes plastic deformation of the cross-direction fibers and consolidation of the web such that a majority of the fibers are aligned generally in the direction of draw (machine direction). The web is consolidated in the cross-direction as it is longitudinally elongated and heat set with respect to the starting nonwoven.

Necked nonwoven substrates having an elongation in the cross-direction of at least 30%, preferably at least 50% can be used to prepare the elastic nonwoven sheet of the current invention. The percent neckdown of the nonwoven web during the consolidation process is preferably between about 50% and about 75%, more preferably between about 60% and 70%, corresponding to an extensibility between about 100% and 300%, and 150% and 250%, respectively.

The basis weight of the necked nonwoven web can be 3 times or more higher than the basis weight of the starting neckable nonwoven web. Preferably, the basis weight of the necked web is between about 15 g/m² and about 70 g/m², more preferably between about 20 g/m² and about 70 g/m², and most preferably between about 25 g/m² and about 70 g/m². The basis weight of the necked nonwoven substrate is chosen according to the desired end use. For example, when used as elastic interliners the basis weight of the necked nonwoven is preferably between about 30 g/m² and 70 g/m² whereas for hygiene end uses such as diaper waistbands, etc. the basis weight is preferably between about 15 g/m² and 40 g/m². The basis weight of the necked nonwoven substrate should also be selected to achieve the desired elasticity in the final impregnated nonwoven. Higher basis weight nonwoven substrates allow more elastomeric polymer to be impregnated into the nonwoven, increasing the unload force of the impregnated nonwoven sheet.

Use of relatively low basis weight nonwovens in the necking process described in Hassenboehier is preferred for preparing materials made according to this invention. Used together, and after impregnation with an elastomeric polymer, these factors combine to provide stretchable nonwovens with a relatively low force required to extend the material (load force) and a relatively high retractive force exerted by the material as it is allowed to relax (unload force). This characteristic is preferred for end uses envisioned for this material. The relationship of unload force to load force is related to the hysteresis of the elastic nonwoven. For the preferred products of the current invention, having a cross direction percent elongation of at least 150%, the ratio of the unload force at 100% elongation to the load force at 100% elongation, after the impregnated nonwoven has been extended to 140% three times and allowed to relax between extensions, is at least 0.3:1 and preferably greater than 0.45:1.

Elastomeric polymers useful in this invention include polyurethanes, styrene-butadiene block copolymers, and polyether-ester block copolymers. In a preferred embodiment, the elastomeric polymer is a polyurethane.

Elastomeric polyurethanes useful in this invention can be prepared by reacting a polymeric glycol with a diisocyanate to form a capped glycol, dissolving the capped glycol (in a suitable solvent), and then reacting the capped glycol with a difunctional chain extender having active hydrogen atoms. Such polyurethanes are termed "segmented" because they are comprised of "hard" urethane and urea segments derived from the diisocyanate and chain extender and "soft" segments derived primarily from the polymeric glycol. Suitable solvents for preparing solutions of such polymers are amide solvents such as dimethylacetamide ("DMAc"), dimethylformamide ("DMF"), and N-methyl-pyrrolidone, but other solvents such as dimethylsulfoxide and tetramethylurea can also be used.

Polymeric glycols used in the preparation of the elastomeric polyurethanes include polyether glycols, polyester glycols, polycarbonate glycols and copolymers thereof. Examples of such glycols include poly(ethyleneether)glycol, poly(tetramethyleneether)glycol, poly(tetramethylene-co-2-methyl-tetramethyleneether)glycol, poly(ethylene-co-butylene adipate)glycol, poly(2,2-dimethyl-1,3-propylene dodecanoate)glycol, poly(pentane-1,5-carbonate)glycol, and poly(hexane-1,6-carbonate)glycol.

Useful diisocyanates include 1-isocyanato-4-[(4-isocyanatophenyl)methyl]benzene, 1-isocyanato-2-[(4-isocyanato-phenyl)methyl] benzene, isophorone diisocyanate, 1,6-hexanediisocyanate, and 2,4-tolylene diisocyanate.

The chain extender can be a diol or a diamine. Useful diols include ethylene glycol, 1,3-trimethylene glycol, 1,4-butanediol, and mixtures thereof. Use of diol chain extenders leads to polyurethanes. Useful diamines include ethylene diamine, 1,2-propanediamine, 2-methyl-1,5-pentanediamine, 1,3-diaminopentane, 1,4-cyclohexane-diamine, 1,3-cyclohexanediamine, and mixtures thereof. In this case, the polymer produced is a polyurethaneurea (a sub-class of polyurethanes). When a polyether glycol and a diamine chain extender are utilized, the polymer produced is a polyetherurethaneurea; when a polyester glycol is utilized in combination with a diamine chain extender, a polyesterurethaneurea is produced. Monofunctional amine chain terminators such as diethyl amine, butylamine, cyclohexylamine, and the like can be added to control the molecular weight of the polymer. In a preferred embodiment, the elastomeric polymer is a diamine-extended polyurethane elastomer.

Solvents suitable for preparing the elastomeric polymer solutions include dimethylacetamide, dimethylformamide, and N-methyl-pyrrolidone. The viscosity of the elastomeric polymer solution is directly related to the concentration of the polymeric material in solution and consequently, the solution viscosity can influence both the degree of penetration of the polymer into the necked nonwoven fabric and the amount of polymer deposited therein. When the solution viscosity is too low, insufficient amounts of elastomer may be deposited in the necked nonwoven substrate resulting in low unload force. When the solution viscosity is too high, penetration of the solution into the nonwoven substrate may be reduced, thereby resulting in incomplete or nonuniform impregnation of the polymer into the nonwoven or formation of a layer of the polymer on the surface of the necked nonwoven. The solution of elastomeric polymer to be impregnated into the necked nonwoven substrate preferably has a solution viscosity of approximately 1000–300,000 centipoise ("cPs"), more preferably 10,000–40,000 cPs. The solution can comprise about 5 wt % to 20 wt % polymer.

It is necessary that the necked nonwoven substrate is able to absorb the polymer solution and that the polymer solution substantially completely and uniformly impregnate the nonwoven substrate. The necked nonwoven substrate should therefore not be coated or otherwise treated in such a way as to prevent the polymer solution from being absorbed into the necked nonwoven fabric. The elastomeric polymer solution and/or the nonwoven fabric can include a surface-active agent to facilitate the impregnation of the web by the polymeric solution. Suitable surface-active agents include non-ionic wetting agents such as polymeric surfactants.

Additives, for example, pigments, antioxidants, ultraviolet light stabilizers and lubricants, can be added in small quantities to the elastomeric polymer solution, provided such additives do not detract from the benefits of the invention.

The elastomeric polymer solution may contain dispersed therein very short, fine fibers, such as cellulose fibers from wood pulp, cotton dust, or other synthetic or natural fibers having a length less than about 0.10 inches (2.5 mm), preferably less than 0.5 mm. The fibers are preferably small enough to fully penetrate the nonwoven fabric during the impregnation step. The short fibers can be added to the polymeric solution in amounts sufficient to deposit between about 3 and about 12 weight percent of short fibers in the impregnated nonwoven sheet, calculated based on the total weight of the nonwoven/elastomeric polymer composite. The short fibers are preferably added to the elastomeric polymer solution at between about 10 and about 30 weight percent, more preferably between about 10 and about 20 weight percent, based on the total weight of the short fibers, elastomeric polymer, and solvent. Nonwoven sheets of the invention which have been prepared by impregnating a necked nonwoven fabric with an elastomeric polymer solution containing powdered cellulose may have a softer hand than those prepared using impregnating solutions which do not contain short fibers. An example of a very fine fiber particulate material suitable for use in the polymer solutions is powdered cellulose available under the trade name "Arbocel 30" available from J. Rettenmaier USA (Schoolcraft, Mich.).

Any suitable method of coating the elastomeric polymer solution onto the necked nonwoven substrate or otherwise impregnating the necked nonwoven substrate can be used as long as the fabric is uniformly impregnated and the coating is not concentrated on one or the other surface of the necked nonwoven substrate. It should be noted that, although coating methods may be employed to treat the necked nonwoven substrate with the elastomeric polymer solution, the solution and nonwoven properties and the coating process conditions are selected such that the polymer solution completely wets the necked nonwoven substrate or is otherwise completely absorbed into or driven into the nonwoven substrate so that a polymeric layer is not formed on either surface of the nonwoven substrate. In general, the amount of polymeric solution applied during coating can be controlled by utilizing a coating implement held at a predetermined distance above the necked nonwoven fabric. The solution can also be mechanically pressed into the necked nonwoven substrate. Rollers, platens, scrapers, knives, and the like can be used in the process of this invention as coating implements. Spraying the solution onto the necked nonwoven substrate can also be effective provided that the elastomeric solution substantially completely and uniformly impregnates the nonwoven substrate. The force of the spray can be adjusted to assist in obtaining good penetration. The necked nonwoven substrate may be impregnated with the elastomeric polymer solution using a process known in the art as a "dip and squeeze" method in which the fibrous web is dipped or otherwise immersed into a tank containing the elastomeric polymer solution followed by squeezing, such as between nip rolls, to remove excess polymer solution. This method is preferred in order to minimize differences between the two surfaces of the stretchable composite nonwoven sheet.

The necked nonwoven substrate is impregnated with sufficient polymer solution to provide the desired unload/load force ratio in the final impregnated nonwoven sheet. The necked nonwoven substrate is preferably impregnated with sufficient polymer solution to deposit therein between about 15 and about 55 weight percent elastomeric polymer, more preferably between about 30 and about 50 weight percent of elastomeric polymer, based on the total weight of elastomeric polymer and nonwoven substrate. When the amount of elastomer is too low, the ratio of unload force to load force can be undesirably low, and when the amount of elastomer is too high, the hand of the surfaces of the sheet can be undesirably tacky. The solution concentration and/or the amount of solution impregnated into the necked nonwoven fabric can be adjusted to achieve the desired polymer content in the impregnated sheet. For example, it was observed that using lower polymer concentration in the solution while retaining a similar elastomer content on the impregnated sheet by using a wider gap between nip rolls during application of the solution gave a product having an improved balance of hand and unload/load force ratio.

Once the nonwoven substrate has been impregnated with a solution comprising a solvent and an elastomeric polymer, the solvent is removed. The solvent is removed by wet coagulation followed by removal of the coagulating liquid. Wet coagulation provides a product having a surprisingly softer, more cloth-like hand than thermal drying. Wet coagulation processes are well known in the art and are commonly used in the production of artificial leathers. Water is preferred as the coagulating liquid due to ease of handling and low cost. Other suitable coagulating liquids include methanol, ethanol, isopropanol, acetone, or methylethyl ketone. A solvent for the elastomeric polymer such as dimethylformamide, dimethylacetamide, or N-methyl-pyrrolidone or other additives such as surfactants may be added to the coagulating liquid to modify the rate of coagulation. In addition, the temperature of the coagulation bath can be controlled to change the coagulation rate. Slower coagulation rates give the impregnated nonwoven a more attractive hand after the solvent has been removed.

In the impregnated nonwoven sheet of the current invention, the elastomeric polymer phase uniformly distributed throughout the necked nonwoven substrate is breathable. Also, the impregnated nonwoven sheet is preferably moisture vapor permeable.

The hand of the impregnated nonwoven sheet can be improved by sanding or napping to raise fibers on the surface of the impregnated sheet resulting in a softer hand. Napping involves passing a fabric over a rotating roll that contains small metal points that effectively brush the fabric to raise fibers to the surface. In sanding, the metal brush is replaced with a rotating roll coated with sandpaper. Preferably, the impregnated fabric is napped or sanded on both surfaces. For example, the fabric can be sanded with 80 to 200 grit sandpaper.

The stretchable impregnated nonwoven sheets of the current invention preferably have a basis weight between about 40 g/m$^2$ and about 100 g/m$^2$. They are especially useful in the waistbands or side panels of diapers and other disposable personal hygiene garments. Diapers are assembled commercially on long, high-speed lines in which the various diaper components are preferably added in the machine direction to avoid slowing of the process. This is particularly true of elastomeric materials, which are normally stretched prior to insertion. A diaper generally includes about 20 or more individual components which must all be placed precisely in the right location on the diaper during the high-speed manufacturing process. This is much easier to achieve if the component (tape, sheet, fiber, etc.) is fed in the same direction in which the diaper is moving. To add components in the cross direction (e.g. a waistband), it is preferable that the material itself stretches in the cross-direction so that it can be fed into the diaper making process as a tape in the machine direction. For example, this tape may be a 7 inch wide and only 1 inch long piece that is cut from a sheet and glued to a diaper or other disposable undergarment. In such processes, it is also preferred that the diaper component being fed into the process be substantially inextensible in the machine direction to facilitate feeding into the process. The stretchable nonwoven sheets of the current invention are substantially inextensible in the machine direction and have a high degree of recoverable stretch in the cross-direction, making them particularly suitable for use in such a process.

TEST METHODS

Basis Weight

A rectangular sample of nonwoven sheet approximately 1.0 inch by 8.0 inches (2.54 cm by 20.32 cm) is relaxed with care so that the sample contains no puckers or wrinkles. The length and width of the sample are measured to the nearest millimeter and the sample is weighed to the nearest tenth of a milligram. The weight is divided by the calculated area and the result expressed in terms of grams per square meter to the nearest 0.1 gram.

Load and Unload Force Analysis

This analysis was performed on an Instron Model 5565 equipped with the Merlin data collection software system. Both the Merlin system and instrument hardware are available from Instron Corporation (Braintree, Mass.). A one inch +/−0.05 inch wide (2.54 cm+/−0.13 cm) and approximately 8 inch (20.32 cm) long sample of a nonwoven sheet is clamped in the jaws of the Instron machine with a sample length set at 3.00 inches (7.62 cm). The sample is prepared such that the length of the sample is aligned with the cross-direction of the nonwoven. The sample is elongated at a rate of six inches per minute (15.24 cm/min) to an elongation of 140%, and then relaxed to its original length. This is repeated two more times and on the third cycle the force exerted by the material on the extension cycle (Load Force) is recorded at 50%, 100% and 135% elongation based on the original sample length and similarly, the force exerted by the material on the third relaxation cycle (Unload Force) is also recorded at the same elongation points. Results are expressed as Third Cycle Load and Unload forces, in grams, at the appropriate percent elongation.

Percent Elongation Analysis

A relaxed strip of nonwoven fabric 1.0 inch (2.54 cm) wide and approximately 8 inches (20.32 cm) long that is free of puckers or wrinkles is marked with a pen at two points 4.0 inches (10.2 cm) apart such that the marks are approximately equal distance from the ends of the fabric. The ends of the fabric are then firmly held by the thumb and forefinger of each hand and the sample is fully extended, but not extended so far that the sample is torn or suffers any similar mechanical damage. The point of maximum elongation is apparent to the person performing the test as a noticeable increase in resistance to extension by the fabric. The length between the two marked points on the nonwoven is then measured and the percent elongation calculated by the following formula, where the initial length is 10.2 cm:

$$\text{Percent Elongation} = \{(\text{elongated length} - \text{initial length})/\text{initial length}\} \times 100\%$$

When the percent elongation is measured in the necked direction, the fabric sample is cut with the length aligned with the cross-direction (necked direction).

EXAMPLE

A 30 inch (76.2 cm) wide, 15 g/m² wettable spunbond polypropylene nonwoven manufactured by Avgol Nonwovens, Israel, was fed through a nip roll at 89 feet per minute (27 m/min) and passed through a 72 inch (1.83 m) long forced air oven at 290° F. (143° C.) to a second nip roll operating at 115 feet per minute (35 m/min) and then onto a take up roll. In this process, the 30 inch (76.2 cm) wide nonwoven was uniformly and smoothly consolidated ("necked") in the cross direction to a width of 10 inches (25.4 cm). It could be extended back to its original 30 inch (76.2 cm) cross-directional width by application of minimal force. The necked nonwoven had essentially zero machine direction elongation and a basis weight of 32.0 g/m².

The necked nonwoven was coated on one surface with a 15 mil (0.38 mm) doctor knife and a dimethylacetamide (DMAC) solution of 20% by weight of a polyurethaneurea derived from 1800 molecular weight poly(tetramethyleneether)glycol, 1-isocyanato-4-[(4-isocyanatophenyl)methyl]benzene (1.69 mole ratio of diisocyanate to glycol), chain extenders (ethylene diamine and 2-methyl-1,5-pentanediamine in a 9:1 mole ratio), and diethylamine. The following additives were also used: 0.5 wt % of a polymer of bis(4-isocyanatocyclohexyl)methane) and (3-t-butyl-3-aza-1,5-pentanediol) (Methacrol® 2462B, a registered trademark of E.I. du Pont de Nemours and Company), 0.3 wt % titanium dioxide, 0.6 wt % silicone oil, 1.4 wt % 2,4,6-tris(2,6-dimethyl-4-t-butyl-3-hydroxybenzyl)isocyanurate (Cyanox® 1790, a registered trademark of Cytec Industries), and 4 wt % of a mixture of huntite and hydromagnesite). (All percentages based on polyurethaneurea weight.) The polyurethaneurea-DMAC solution fully wet the nonwoven.

The coated nonwoven was suspended substantially vertically in air for approximately 1 minute to allow full penetration of the polymer solution into the nonwoven and then immersed in a 70° F. (21° C.) bath of 40% by volume DMAC in water. After one minute, the impregnated fabric was successively transferred to 30 volume %, 20 volume % and 10 volume % DMAC/water solutions for one minute each and finally immersed in a 100% water bath for 2 minutes. The impregnated fabric was dried in air at room temperature.

The resulting impregnated nonwoven sheet had equivalent (dry, textile-like) hand and texture on both surfaces. Photomicrographs of the cross-section of the impregnated nonwoven sheet indicated a uniform composite structure through the thickness of the material and substantially no areas of continuous polyurethane on either surface.

The nonwoven sheet was then lightly sanded with a 220 grit sand paper. The resulting material had a noticeably softer feel and visual observation showed numerous individual short fibers projecting from the surface compared to a completely smooth surface with no projecting fibers prior to sanding. It was unexpected that this treatment succeeded in giving a softer hand without significantly impairing the visual aesthetics or the elastic characteristics of the sheet.

The resulting impregnated nonwoven sheet had a basis weight of 71.4 g/m², indicating a polyurethaneurea content of 39.4 grams per square meter, or approximately 55 weight % elastomeric polymer.

Hand elongation of the resulting material in the cross-direction indicated an elongation of between about 160% and 180%. Load and Unload Force analysis gave the following results:

| Third Load Cycle Force | |
|---|---|
| % Elongation | Load force in grams |
| 50 | 67.3 |
| 100 | 211.2 |
| 135 | 409.7 |

| Third Unload Cycle Force | |
|---|---|
| % Elongation | Unload force in grams |
| 50 | 22.7 |
| 100 | 114.7 |
| 135 | 340.7 |

Comparison of the data in the tables indicates that the ratio of unload force to load force at 100% elongation was 0.54.

What is claimed is:

1. A method for forming a stretchable nonwoven sheet comprising the steps of:
   providing a necked nonwoven substrate having a thickness, first and second outer surfaces, a machine direction and a cross-direction, the necked nonwoven substrate having an percent elongation of at least 30% in the cross-direction;
   substantially uniformly impregnating the necked nonwoven substrate with a solution comprising an elastomeric polymer dissolved in a solvent; and
   removing the solvent from the impregnated nonwoven substrate by wet coagulation to deposit the elastomeric polymer substantially uniformly throughout the thickness of the nonwoven substrate without forming a substantially continuous layer of elastomeric polymer on either of the first or second outer surfaces of the nonwoven substrate.

2. The method according to claim 1 wherein the necked nonwoven substrate has a percent elongation of less than about 5% in the machine direction and a percent elongation in the cross-direction of between about 100% and about 300%.

3. The method according to claim 1 wherein the necked nonwoven substrate is a necked nonwoven fabric having a basis weight between about 15 g/m² and about 70 g/m².

4. The method according to claim 1 wherein the elastomeric polymer is a polyurethane.

5. The method according to claim 1 wherein the elastomeric polymer is deposited on the substrate at about 15 to 55 weight percent based on the combined weight of the substrate and the elastomeric polymer.

6. The method according to claim 1 further comprising a step of sanding or napping at least one of the outer surfaces of the nonwoven sheet after the solvent has been removed to raise fibers on the surface of the sheet.

* * * * *